United States Patent [19]

Hashizume et al.

[11] Patent Number: 4,593,122
[45] Date of Patent: Jun. 3, 1986

[54] PROCESS FOR PREPARING TEREPHTHALIC ACID BY THE CATALYTIC OXIDATION WITH AIR OF P-XYLENE IN A WATER CONTAINING ACETIC ACID SOLVENT

[75] Inventors: Hiroshi Hashizume, Kurashiki; Yoshiaki Izumisawa, Kitakyushu, both of Japan

[73] Assignee: Mitsubishi Chemical Industries Limited, Tokyo, Japan

[21] Appl. No.: 635,264

[22] Filed: Jul. 27, 1984

[30] Foreign Application Priority Data

Aug. 9, 1983 [JP] Japan ................. 58-145407

[51] Int. Cl.⁴ .......................... C07C 51/265
[52] U.S. Cl. ................. 562/414
[58] Field of Search ................. 562/414

[56] References Cited

U.S. PATENT DOCUMENTS 3,086,993  4/1963  Bulkley et al. ............. 562/414
3,534,090  10/1970  Bryant, Jr. et al. .......... 562/414

FOREIGN PATENT DOCUMENTS 38075  11/1973  Japan .
 1301  1/1981  Japan .

Primary Examiner—Natalie Trousof
Assistant Examiner—Patricia M. Scott
Attorney, Agent, or Firm—Oblon, Fisher, Spivak, McClelland & Maier

[57] ABSTRACT

A process for producing terephthalic acid from p-xylene continuously, wherein p-xylene is oxidized to terephthalic acid by air in the presence of a catalyst containing cobalt, manganese and bromine at a temperature of 180° to 230° C. in a water containing acetic acid solvent in which the concentration of oxygen gas contained in an exhaust gas obtained from the reaction vessel used for oxidizing p-xylene is 2 to 8% by volume, said process comprising, (a) preparing an oxidation exhaust gas by condensing a gas withdrawn from said reaction vessel for removing condensates from said gas, (b) dividing the prepared oxidation exhaust gas into a discharged gas and a recycled gas, in which the volume ratio of said recycled gas to said discharged gas is 0.3 to 5, said discharged gas being exhausted to the outside of the reaction system, (c) supplying continuously said recycled gas to the liquid phase of said reaction vessel, and (d) carrying out the oxidation reaction of p-xylene under reaction pressure higher than the pressure of the reaction system when gas is not recycled to the system.

9 Claims, 1 Drawing Figure

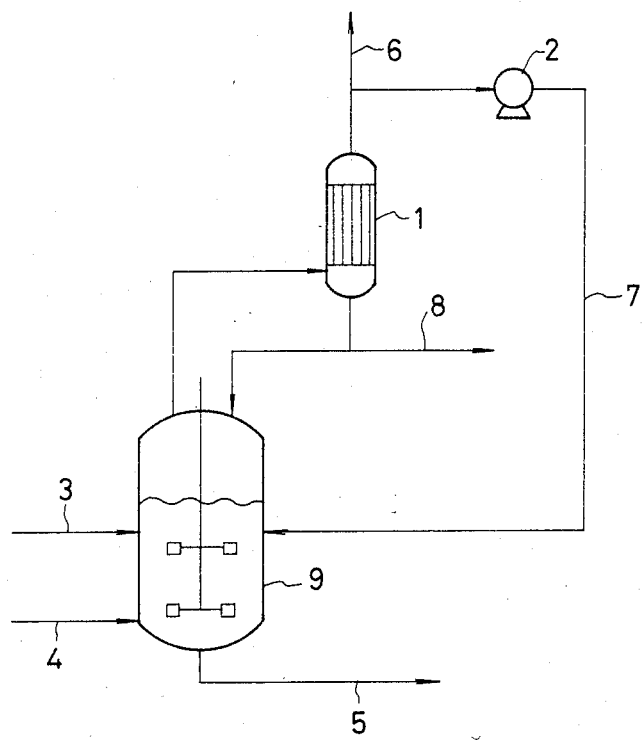

PROCESS FOR PREPARING TEREPHTHALIC ACID BY THE CATALYTIC OXIDATION WITH AIR OF P-XYLENE IN A WATER CONTAINING ACETIC ACID SOLVENT

The present invention relates to a process for producing terephthalic acid(hereinafter referred to as TPA), and more in detail, particularly to a process for producing TPA of an excellent transmissivity.

TPA is important as one of the starting materials of polyester and is industrially produced by the so-called SD process in which p-xylene is oxidized by air in a liquid phase containing acetic acid as a solvent in the presence of a catalyst including cobalt, manganese and bromine. However, TPA produced by SD process is unsuitable for a starting material for producing, for instance, polyester commercially used for fibers or films, since the purity of TPA is not sufficient therefor. Namely, in the case where TPA produced by SD process is used for producing polyester without any purification thereof, it is impossible to obtain polyester having a commercially satisfactory colour tone. Although it is not sufficiently made clear that each of the impurities contained in TPA used for a starting material affects the colour tone of the polyester prepared from TPA containing the same, the quality of TPA is empirically determined mainly by the transmissivity of TPA itself and the content of 4-carboxybenzaldehyde(hereinafter referred to as 4CBA) which is one of the intermediate compounds in the process for producing TPA from p-xylene. Even now where the polymerization technique has been much progressed, it is required in view of industrial production that a content of 4CBA in TPA is less than 500 ppm and transmissivity($T_{340}$) of TPA is higher than 85%, though required quality of TPA may be different respectively according to the aimed quality of polyester. Accordingly, the crude TPA produced hitherto by SD process is further purified in separate purifying plant and then the purified TPA is used as the starting material for polyester. For example, the conventional method for purifying the crude TPA comprises esterifying the crude TPA with methanol and purifying methyl ester of TPA, or comprises dissolving the crude TPA in water and purifying the dissolved crude TPA by reduction under a high pressure at a high temperature in the presence of palladium catalyst.

In addition, in recent years, a single producing plant for TPA having a high purity has been developed by the improvement of the reaction condition and the reaction process in SD process and, in the single plant, it is not necessary to install a separate purifying plant of the crude TPA. The produced TPA having a high purity can be used as a starting material for polyester. In the concrete, it is publicly known that p-xylene is oxidized according to SD process under the specific condition and the resultant reaction mixture containing TPA is further oxidized at a temperature lower than that of the first oxidation or in addition, the further oxidized mixture may be moreover oxidized at a temperature higher than that of the first oxidation.

According to each of the processes with a single plant, TPA having a high purity can be obtained at an extremely low cost as compared to the cost of the case where a separate purifying plant is necessitated to remove impurities contained in the crude TPA. The purity of the produced TPA by plural oxidations is in the permissible range of which the amount of the impurities does not affect the quality of polyester in view of the present technical level of polymerization of polyester even if the purity of the produced TPA by plural oxidations is a little inferior to that of TPA obtained by a single oxidation process in which a separate purifying plant is necessitated as mentioned above, provided that the content of 4CBA of the thus produced TPA is less than 500 ppm and the transmissivity ($T_{340}$) thereof is higher than 85%. In general, if the transmissivity of this kind of TPA is sufficiently high, it does not hurt the colour tone of the polyester prepared therefrom that the content of 4CBA is a little higher than the normal content level of 4CBA. However, according to the conventional technical level of producing TPA, in order to produce TPA having a high transmissivity, it is necessary to produce TPA having a considerably low content of 4CBA. In other words, it has been inevitable to decrease excessively the content of 4CBA in order to raise the transmissivity of TPA, although the content of 4CBA is within an allowable range.

In addition, the quality of TPA can be generally controlled by selecting the conditions of oxidation such as the resident time of the reactant in the reactor, the amount of catalyst, the reaction temperature and the like of the main oxidation, the reaction conditions of the first additional oxidation and/or the second additional oxidation. Generally, in the case of producing TPA of a low content of 4CBA, the process has a tendency toward the larger loss of acetic acid as a solvent due to combustion thereof and therefore, the cost of producing TPA is raised. Accordingly, if it is possible to improve the transmissivity of TPA by a simple method other than the conventional techniques and to raise the content of 4CBA from the present level concerning 4CBA contained in TPA now dealing with commercially, TPA having a high purity may be produced at a lower cost than that of the conventional process.

In consideration of the present status of the production of TPA, the present inventors have examined various processes for producing TPA particularly excellent in the transmissivity and as a result, the present inventors have found out that it is possible to obtain a reaction mixture containing TPA excellent in the transmissivity by oxidizing p-xylene under an increased partial pressure of oxygen in the gas phase of the reaction system by the use of a specific method; TPA having a transmissivity ($T_{340}$) of higher than 85% to be aimed is obtained by subjecting the obtained reaction mixture to the additional oxidative treatment, even if the content of 4CBA therein is higher than 500 ppm; even in the case where polyester is prepared directly from the obtained TPA, a polyester having an excellence of the colour tone can be obtained; and in the case where the oxidation of p-xylene is carried out under the conditions to attain the same level of the content of 4CBA as in the conventional conditions of the oxidation (for instance, 200 to 300 ppm), the transmissivity ($T_{340}$) of the obtained product becomes to about 95% and, in other words, it is possible to produce TPA of an exceptionally high quality for use in preparing a special grade of polyester. The present inventors have accomplished to the present invention based on the knowledges mentioned above.

It is an object of the present invention to provide a process for producing terephthalic acid from p-xylene continuously, wherein p-xylene is oxidized into terephthalic acid by air in the presence of a catalyst containing cobalt, manganese and bromine at a temperature of 180° to 230° C. in acetic acid solvent in which the concentration of oxygen gas contained in an exhaust gas from the reaction vessel used for oxidizing p-xylene is 2 to 8% by volume, said process comprising (a) condensing a gas drawn out from said reaction vessel for removing condensates from said gas thereby to prepare an oxidation exhaust gas, (b) dividing the prepared oxidation exhaust gas into a discharged gas and a recycled gas, in which the volume ratio of said recycled gas to said discharged gas is 0.3 to 5, said discharged gas being exhausted to outside of the reaction system, (c) supplying continuously said recycled gas to the liquid phase of said reaction vessel, and (d) carrying out the oxidation of p-xylene under a reaction pressure higher than the pressure of the reaction system when no gas is recycled to the same.

In the drawing, the single figure is a diagrammatic illustration of the reaction vessel for main oxidation of p-xylene.

Hereinafter, the present invention is described more in detail.

In the present invention, any process for producing TPA continuously in which p-xylene is oxidized by an oxygen-containing gas in a liquid phase containing acetic acid as a solvent in the presence of a catalyst containing cobalt, manganese and bromine, may be utilized. The process of the present invention can produce either TPA having a high purity which can be directly used as a starting material for preparing polyester or crude TPA which is necessary to purify in the subsequent procedure. In the case where the present invention is applied to the production of the TPA having a high purity, it is possible to obtain an excellent TPA in transmissivity even though the content of 4CBA therein is higher than the level of the product commercially utilized hitherto. Moreover in the case where the content of 4CBA is made to the same level as in the conventional product, it is possible to produce TPA having an extremely high transmissivity which has never been obtained unless the conventional TPA is further treated in a separate purifying plant. In addition, in the case where the present invention is applied to the production of the crude TPA, it is possible to reduce the load on the purifying plant of the crude TPA, since the obtained crude TPA has an excellent transmissivity in its own way.

The amount of acetic acid used as a solvent in the process of the present invention is generally 2 to 6 parts by weight to one part by weight of p-xylene used therein and acetic acid used as a solvent may contain less than 10% by weight of water. Oxygen gas contained in air used in the process of the present invention may be diluted or concentrated and in general the amount of air used therein is 15 to 40 parts by mole to one part by mole of p-xylene.

The catalyst used in the process of the present invention contains cobalt, manganese and bromine, respectively as the indispensable component and for example as the source of these components, cobalt acetate, cobalt naphthenate, cobalt bromide and the like as a cobalt compound; manganese acetate, manganese naphthenate, manganese bromide and the like as a manganese compound; and hydrogen bromide, sodium bromide, cobalt bromide, manganese bromide and the like as a bromine compound may be mentioned. The amount of the cobalt compound used in the process of the present invention is generally 100 to 3000 ppm, preferably 150 to 2000 ppm as a cobalt atom in a solvent. Generally, the manganese compound is used in an amount so that the atomic ratio of manganese to cobalt in the catalyst is in a range of from 0.05 to 2. The bromine compound is used in an amount so that the atomic ratio of bromine to cobalt in the catalyst is generally in a range of from 2 to 5. Furthermore, the catalyst according to the present invention may contain other components than cobalt, manganese and bromine.

The oxidation in the process of the present invention is generally carried out at a temperature of 180° to 230° C., preferably 180 to 220° C. and under a pressure higher than the pressure under which the reaction mixture can be maintained in liquid phase at the reaction temperature. In generally, the reaction pressure is 8 to 50 kg/cm² G. Although the reaction time period depends upon the size of the apparatus and other reaction conditions, it is 30 to 180 min in general. The water content within the reaction system is generally 5 to 20% by weight of the content therein, preferably 7 to 14% by weight. For example, the water content in the reaction system can be controlled by the conventional method in which the exhaust gas from the reaction vessel is condensed to prepare a reflux condensate and a part of the prepared reflux condensate is purged to the outside of the reaction system.

The reactor used in the process of the present invention is, in general, a type of the vessel provided with a stirrer, a reflux condenser at the top thereof and also an air-supplying inlet on the bottom part thereof. The air supplied from the air-supplying inlet is utilized in oxidation reaction of p-xylene and then is drawn out from the reaction vessel while accompanying a large amount of vapour of acetic acid and water as main components. After condensing and removing the vapour contained therein, the utilized air is discharged as the exhaust gas of oxidation. The condensate recycled to the reaction vessel and, in the case where it is necessary to control the water content within the reaction system, a part of the condensate is purged to the outside of the reaction system.

The reaction temperature in the process of the present invention is controlled by regulating the amount of vaporization of acetic acid and water as main components from the liquid phase within the reaction vessel. Concretely, the regulation of the amount of vaporization of them is carried out by changing the amount of supplied air or of the reaction pressure. In the case where the oxidation process of the present invention is carried out industrially, it is necessary to control the amount of supplied air in view of explosion limit so that the content of oxygen gas in the exhaust gas of oxidation is in a range from 2 to 8% by volume, preferably from 4 to 7% by volume. Accordingly, if the reaction pressure is simply raised in order to raise the partial pressure of oxygen in the gas phase of the reaction system, the heat balance in the reaction system is broken up and the reaction temperature is raised.

According to the present invention, the reaction pressure is raised by recycling a specific amount of the oxidation exhaust gas discharged from the reaction vessel to the liquid phase in the reaction vessel and as a result, it is possible to raise the partial pressure of oxygen gas in the gas phase of the reaction system to a higher level than the pressure in the case where the oxidation exhaust gas is not recycled and it is possible to control the reaction temperature by controlling the amount of the recycled gas without exerting serious influence on the other reaction conditions. The reaction pressure is generally controlled to give the partial pressure of oxygen of 1.3 to 5 times, preferably 1.5 to 3 times as high as the partial pressure of oxygen gas in the case of not recycling the oxidation exhaust gas and the molar ratio of the non-condensable gas to the condensable gas in the gas phase in the reaction vessel (hereinafter referred to as the ratio of inert pressure to vapour pressure) is controlled in the range of from 0.65 to 3, preferably in the range of from 0.7 to 2. Further, the amount of the recycled gas is controlled to a level which will be described later. Although the ratio of the inert pressure to vapour pressure in the conventional method is nearly 0.5, the ratio can be raised optionally according to the process of the present invention. In the case where the oxidation is carried out by air at a predetermined temperature, the reaction pressure and the partial pressure of oxygen in the gas phase of the reaction system are determined by setting the concentration of oxygen in the oxidation exhaust gas. On the other hand, the process of the present invention can raise the partial pressure of oxygen to a level higher than the partial pressure determined as above and as a result, it is possible to obtain TPA excellent in the transmissivity.

The gas drawn out from the reaction vessel contains condensable components such as acetic acid, water, methyl acetate and the like and the oxidation exhaust gas obtained by removing such condensable components therefrom is divided into the two gas flows, that is, one of which is discharged to the outside of the reaction system as a discharged gas and the other of which is recycled into the reaction vessel as a recycled gas. As has been described, the volume ratio of the recycled gas to the discharged gas is set in a range of from 0.3 to 5, preferably in the range of from 0.5 to 3.

The gas flow to be discharged to the outside of the reaction system may be optionally subjected to an additional condensation treatment for removing condensable components and then, the treated gas is discharged to the outside of the reaction system as a discharged gas and also, if necessary, the gas flow to be recycled into the reaction vessel may be subjected to an additional condensation treatment for removing condensable components therein and the treated gas is supplied to the reaction vessel as a recycled gas. In the case where the recycled amount of the oxidation exhausted gas is not in the range mentioned above, it is difficult to sufficiently raise the partial pressure of oxygen within the reaction system and accordingly, TPA excellent in transmissivity is hardly obtained. Usually, the oxidation exhaust gas having high pressure, which has been subjected to a condensation treatment for removing acetic acid and water, is preferably used as a recycled gas. In the case where the pressure of the oxidation exhaust gas has been reduced to a level of atmospheric pressure, it is necessary to raise the pressure thereof for supplying into the reaction vessel and such a procedure is industrially not desirable. The position of the inlet through which the recycled gas is introduced into the reaction vessel is preferably lower than the surface of the liquid phase preferably lower than 1/5 of the height of the liquid phase from the surface of the liquid. In addition, in the case where the recycled gas is supplied into the gas phase of the reaction vessel, the expected effect as in the present invention is hardly obtained. Further, in the case where the recycled gas is mixed with air and then, the mixture of the recycled gas and air is supplied to the reaction vessel, it is attended with danger of explosion.

Accordingly, these techniques can not be adopted in an industrial process as a practical problem. As a simple method for recycling the oxidation exhaust gas, a blower may be adopted in general, because the pressure of the gas itself to be recycled is about the same as the inner pressure of the reactor.

As has been described above, in the present invention, air is used as the oxidative gas. In the case where the oxidation of p-xylene is carried out under the condition that the concentration of oxygen in the oxidation exhaust gas is maintained at a predetermined level, the reaction pressure can be raised while maintaining the reaction temperature at a constant level by recycling a part of the oxidation exhaust gas into the reaction vessel. Accordingly, it is possible to raise the partial pressure of oxygen gas in the gas phase of the reaction system and as a result, TPA particularly excellent in transmissivity is easily produced by the process of the present invention.

According to the present invention, the oxidation is over and afterwards, the reaction mixture may be subjected to a treatment of crystallization, however, it is preferable to carry out crystallization after subjecting the reaction mixture to the other suitable treatments according to the objective procedures. For instance, the reaction mixture is subjected to a publicly known technical treatment such as the additional oxidation at a lower temperature or the additional two stage oxidation at a lower temperature and then at a higher temperature and the likes.

The treatment of additional oxidation at lower temperature is generally carried out by further oxidizing the original reaction mixture at a temperature lower than that of the original oxidation by 5° to 30° C. while supplying an amount of the oxidative gas 1/10 to 1/1000 times that in the original oxidation for 5 to 120 min. It is preferable that in the reaction mixture subjected to the additional oxidation at a lower temperature, more than 95% by weight of p-xylene which has been supplied to the main oxidation has been converted into TPA.

In the case where the additional oxidation at a higher temperature is carried out in succession to the additional oxidation at a lower temperature, the temperature of the reaction mixture of the second oxidation (that is, the additional oxidation at a lower temperature) is raised to 240 to 280° C. and the pre-heated reaction mixture is further oxidized for 5 to 120 min while supplying the oxidative gas in an amount of 1/5 to 1/500 times as much as the main oxidation. According to the conventional method, the mixture through the additional oxidation(s) is subjected to crystallization treatment and the crystals of TPA is collected by filtration and thereafter, the collected crystals is washed in suspension with acetic acid to obtain TPA excellent in transmissivity.

As has been described above, it is possible to obtain TPA having a high transmissivity according to the process of the present invention and accordingly, in the case where the process of the present invention is applied for production of TPA having a high purity, which is utilizable as the starting material for polyester, a particularly excellent effect is attained. Further, in the case where the process of the present invention is applied for production of the TPA of the same level of transmissivity as the conventional product, the conditions of oxidation can be moderated so that the combustion amount of acetic acid as a solvent is reduced and therefore, the consumption amount of acetic acid is reduced, since a little higher content of 4CBA than that of the conventional process does not cause harm to the product of the present invention. In addition, in the case where the conditions in oxidation is not moderated, it is also possible to obtain TPA of an ultrahigh purity and of an extremely high transmissivity according to the process of the present invention.

Accordingly, the present invention contributes industrially to this field and the economic effect of the present invention may be considerable.

The present invention will be explained more in detail while referring to the non-limitative examples.

In addition, in Examples, "part(s)" means "part(s) by weight".

EXAMPLES 1 TO 4 AND COMPARATIVE EXAMPLES 1 AND 2

Productions of TPA containing about 1000 ppm of 4CBA

The oxidation reaction of p-xylene into TPA was carried out in an apparatus for continuous reaction comprising a main reaction vessel as schematically shown in the attached drawing, a pressure reactor for additional oxidation reaction and a cooling crystalizer. The main reaction vessel was provided with a pressure reaction vessel 9 made of titanium for a main oxidation reaction having a stirrer and a heating apparatus, a reflux condenser 1, a supplying line 3 for p-xylene and a solvent, an air-supplying line 4, drawing out line 5 for a slurry of a reaction mixture, a drawing out line 8 for a refluxed liquid, a blower 2 for recycling an oxidation exhaust gas into the vessel 9, and a recycling line 7. The pressure reactor made of titanium for additional oxidation reaction was provided with a reflux condenser, a stirrer, a heating apparatus, an air-supplying line, a charging inlet for a slurry of the reaction mixture, and a drawing outlet of the resultant mixture. The cooling crystalizer was provided with a reflux condenser, a stirrer, a charging inlet for a slurry of the resultant mixture and a drawing outlet for the cooled mixture.

In the main oxidation, a mixture containing one part of p-xylene, 4.6 parts of acetic acid containing 5% by weight of water, 0.0042 part of cobalt acetate tetrahydrate, 0.0044 part of manganese acetate tetrahydrate and 0.0064 part of an aqueous solution containing 47% by weight of hydrogen bromide was supplied to the reaction vessel 9 via the line 3 at a rate of 5.615 parts/hour. The contents of cobalt, manganese and bromine in the reaction system was 300 ppm, 300 ppm and 900 ppm, respectively on calculation based on the charged components. Air as the oxidative gas was supplied to the vessel 9 via the line 4 so as to make the concentration of oxygen gas in the oxidation exhaust gas to 6% by volume while maintaining the inner pressure of the vessel 9 at a level shown in Table 1 by purging the oxidation exhaust gas coming from the reflux condenser 1 to the outside of the reaction system via the line 6 and by recycling the oxidation exhaust gas at a ratio shown in Table 1 to the vessel 9 from the blower 2 via the line 7 and at the same time, the water concentration in the reaction system was controlled at about 10% by weight by drawing out the recycle liquid from the line 8 at a rate of 1.6 parts/hour. The main oxidation of p-xylene was carried out at a reaction temperature of 190° C. and a residence time of 90 min.

The slurry of the reaction mixture was drawn out from the vessel 9 via the line 5 and was continuously supplied to the reactor for additional oxidation. The additional oxidation was carried out at a temperature of 183° C. under the pressure of 10 kg/cm$^2$ G while supplying air so as to make the concentration of oxygen gas in the oxidation exhaust gas to 6% by volume. The resident time of the reaction mixture to be additionally oxidized was 30 min.

The additionally oxidized mixture having a slurry-like form was sent to the cooling crystallizer and was subjected to crystallizing treatment. Afterwards, the crystals were collected by filtration. After washing the crystals in suspension with acetic acid, the crystals were again collected by filtration and the collected crystals were dried to obtain the crystals of TPA.

The continuous oxidation procedures were carried out for 24 hours and thereafter, the transmissivity of the obtained crystalline TPA and the content of 4CBA therein were measured as well as the determination of the colour tone(b-value) of polyester prepared from the crystalline TPA and the amount of combustion of acetic acid as a solvent in the production of TPA. The results of the measurements are shown also in Table 1.

TABLE 1

| | Amount of recycled exhaust gas[1] | Reaction pressure (kg/cm$^2$G) | Partial pressure of O$_2$ (atm) | Ratio of inert gas pressure to vapour pressure | Transmissivity of TPA (T$_{340}$)[2] (%) | Content of 4CBA in TPA (ppm) | Amount of combusted acetic acid[3] | Colour tone of polyester[4] (b-value) |
|---|---|---|---|---|---|---|---|---|
| Example 1 | 0.5 | 15.5 | 0.42 | 0.77 | 88 | 1050 | 1.0 | 4.8 |
| Example 2 | 1 | 18 | 0.56 | 1.04 | 89 | 1050 | 1.0 | 4.3 |
| Example 3 | 2 | 23 | 0.85 | 1.58 | 90 | 1000 | 1.0 | 4.0 |
| Example 4 | 3 | 30 | 1.26 | 2.33 | 89 | 1100 | 1.0 | 4.5 |
| Comparative Example 1 | 0 | 13 | 0.27 | 0.50 | 75 | 950 | 1.0 | 8.0 |
| Comparative Example 2 | 0.2 | 14 | 0.33 | 0.61 | 82 | 1050 | 1.0 | 6.5 |

Notes for Table 1 (the same in Tables 2 and 3):
[1]Amount of the recycled oxidation exhausted gas is shown as a volume ratio of the amount of the recycled oxidation exhausted gas based on the non-condensable components to the amount of the oxidation exhaust gas purged to the outside of the system.
[2]Transmissivity of TPA is shown as a transmissivity of a solution of 7.5 g of TPA in 50 ml of an aqueous 2N solution of potassium hydroxide to a light of wave length of 340 nm at an optical path of 10 mm in length.
[3]Amount of combusted acetic acid as a solvent: After analyzing the amounts of carbon monoxide and carbon dioxide contained in the oxidation exhaust gas discharged from each of the reactors, the amount of combusted acetic acid in the process was calculated from the measurements. In the results shown, the amount of acetic acid combusted in Comparative Example 1 is taken as the standard, 1.0.
[4]Colour tone of polyester (b-value): After esterifying TPA with ethylene glycol following a publicly known process, the obtained ester was polymerized into a polyester. The colour tone of the prepared polyester was measured by a colour-difference meter (made by Tokyo Denshoku Kogyo Co., Ltd., trade name of model TC-55) and was represented by the b-value. By the way, the b-value with the ideogram (+) means the yellowish tone and that with the ideogram (−) means the bluish tone. In the case of the smaller the value, the colour tone is better.

As are seen from Table 1, even under the same reaction conditions, in the case of recycling a part of the oxidation exhaust gas into the reaction vessel 9, although the content of 4CBA in TPA is the same as in the case of not recycling thereof(as in Comparative Examples), the transmissivity of TPA obtained in Examples of the present invention is considerably higher than that of Comparative Examples.

For instance, in Comparative Example 1 in which the oxidation exhaust gas was not recycled, the content of 4CBA is 950 ppm, the transmissivity is 75% and the colour tone (b-value) of polyester prepared therefrom is 8.0.

From the commercial viewpoint, TPA produced in Comparative Example 1 is unsuitable as a starting material directly used for preparing polyester and accordingly, and additional purification is required. On the other hand, in Example 1, TPA was produced by the same procedures as in Comparative Example 1 except for recycling a part of the oxidation exhaust gas into the reaction system and raising the reaction pressure by about 20% as compared to Comparative Example 1 and as a result, the transmissivity of TPA obtained in Example 1 is considerably improved into 88% in spite of 1050 ppm of 4CBA which is a little larger than that of TPA produced in Comparative Example 1.

Moreover, the colour tone of polyester prepared from TPA produced in Example 1 is very excellent and is b-value of 4.8. This b-value of 4.8 is similar level to the colour tone of polyester commerciallized as a row material for preparing fibers and accordingly, TPA produced in Example 1 can be directly used as the starting material for preparing polyester to be commercialized. According to the present invention, a process for producing a crude TPA can be converted into a process for producing TPA having a high purity under the same conditions except for recycling a part of the oxidation exhaust gas to the reaction system and the industrial value of the present invention can be highly evaluated.

EXAMPLE 5 AND COMPARATIVE EXAMPLE 3

Productions of TPA containing about 1000 ppm of 4CBA

TPA was produced in the same apparatus under the same conditions as in Example 1 except for supplying a catalyst containing 230 ppm of cobalt, 230 ppm of manganese and 690 ppm of bromine and maintaining the reaction temperature at 200° C. in the main oxidation and at 193° C. in the additional oxidation.

The results are shown in Table 2.

TABLE 2

| | Amount of Recycled exhaust gas[1] | Reaction pressure (kg/cm$^2$G) | Partial pressure of O$_2$ (atm) | Ratio of inert gas pressure to vapour pressure | Transmissivity of TPA (T$_{340}$)[2] (%) | Content of 4CBA in TPA (ppm) | Amount of combusted acetic acid[3] | Colour tone of polyester[4] (b-value) |
|---|---|---|---|---|---|---|---|---|
| Example 5 | 1 | 23 | 0.72 | 1.09 | 90 | 1050 | 1.0 | 4.2 |
| Comparative Example 3 | 0 | 16 | 0.32 | 0.49 | 77 | 1050 | 1.0 | 8.2 |

EXAMPLE 6 AND COMPARATIVE EXAMPLE 4

Production of TPA containing about 1000 ppm of 4CBA

TPA was produced in the same apparatus under the same conditions except for supplying a catalyst containing 350 ppm of cobalt, 350 ppm of manganese and 1050 ppm of bromine and maintaining the reaction temperature at 185° C. in the main oxidation and at 178° C. in the additional oxidation. The results are shown in Table 3.

TABLE 3

| | Amount of recycled exhaust gas[1] | Reaction pressure (kg/cm$^2$G) | Partial pressure of O$_2$ (atm) | Ratio of inert gas pressure to vapour pressure | Transmissivity of TPA (T$_{340}$)[2] (%) | Content of 4CBA in TPA (ppm) | Amount of combusted acetic acid[3] | Colour tone of polyester[4] (b-value) |
|---|---|---|---|---|---|---|---|---|
| Example 6 | 1 | 15 | 0.45 | 0.93 | 88 | 950 | 1.0 | 4.6 |
| Comparative Example 4 | 0 | 11 | 0.22 | 0.45 | 74 | 1000 | 1.0 | 7.8 |

EXAMPLE 7 AND COMPARATIVE EXAMPLE 5

Production of TPA containing about 2000 ppm of 4CBA

TPA was produced in the same apparatus under the same conditions as in Example 1 except for using a catalyst containing reduced amounts of the respective components thereof, namely, in concentrations, 230 ppm of cobalt, 230 ppm of manganese and 690 ppm of bromine.

The results are shown in Table 4.

As are seen from Table 4, the effect of the present invention is exhibited in the case where TPA having a content of more than 2000 ppm of 4CBA is produced. TPA obtained in Example 7 shows a little lower transmissivity of 84% and the product cannot be used directly as the starting material for preparing polyester. However, the transmissivity of 84% is a considerably large improvement as compared to that of TPA obtained in Comparative Example 5.

Accordingly, in the case where TPA obtained according to the process of the present invention is treated in a separate purifying plant, it is expected that the load in the purification step is sharply lessened to a large extent.

EXAMPLES 8 AND 9 AND COMPARATIVE EXAMPLES 6 AND 7

Production of TPA containing about 280 ppm of 4CBA

TPA was produced in the same apparatus under the same conditions as in Example 1 except for supplying 5 parts of acetic acid containing 5% by weight of water;

drawing out the recycle liquid from the line (8) at a rate of 2 parts/hour for regulating the water content therein at about 10%; carrying out the main oxidation at 205° C.; and carrying out the additional oxidation at 198° C.

The results are shown in Table 5.

data show the lower production cost of TPA in Example 2 as compared to that of Comparative Example 6.

EXAMPLES 10 AND 11 AND COMPARATIVE EXAMPLES 8 AND 9

TABLE 4

| | Amount of recycled exhaust gas[1] | Reaction pressure (kg/cm$^2$G) | Partial pressure of O$_2$ (atm) | Ratio of inert gas pressure to vapour pressure | Transmissivity of TPA (T$_{340}$)[2] (%) | Content of 4CBA in TPA (ppm) | Amount of combusted acetic acid[3] | Colour tone of polyester[4] (b-value) |
|---|---|---|---|---|---|---|---|---|
| Example 7 | 1 | 18 | 0.56 | 1.04 | 84 | 2200 | 0.7 | 7.0 |
| Comparative Example 5 | 0 | 13 | 0.27 | 0.50 | 64 | 2100 | 0.7 | 11.8 |

TABLE 5

| | Amount of recycled exhaust gas[1] | Reaction pressure (kg/cm$^2$G) | Partial pressure of O$_2$ (atm) | Ratio of inert gas pressure to vapour pressure | Transmissivity of TPA (T$_{340}$)[2] (%) | Content of 4CBA in TPA (ppm) | Amount of combusted acetic acid[3] | Colour tone of polyester[4] (b-value) |
|---|---|---|---|---|---|---|---|---|
| Example 8 | 0.5 | 22 | 0.59 | 0.80 | 94 | 270 | 1.9 | 2.5 |
| Example 9 | 1.0 | 26 | 0.85 | 1.11 | 95 | 280 | 1.9 | 2.5 |
| Comparative Example 6 | 0 | 18.5 | 0.39 | 0.52 | 89 | 270 | 1.9 | 4.3 |
| Comparative Example 7 | 0.2 | 20 | 0.47 | 0.64 | 91 | 290 | 1.9 | 3.8 |

As are seen from Table 5, the effect of the present invention is also exhibited in the case of producing a highly pure TPA containing about 280 ppm of 4CBA, which is directly utilizable as the starting material for preparing polyester. TPA such as the product obtained in Comparative Example 6 has been hitherto handled commercially as a highly pure TPA. In the case where the process according to the present invention is applied for producing such TPA, the obtained TPA (in Example 8) shows a higher transmissivity of 94% and the polyester prepared from the TPA shows an excellent colour tone (b-value) of 2.5.

In other words, in the case of applying the process according to the present invention to the production of a highly pure TPA, it is possible to obtain a ultrahighly pure TPA. By the way, it is possible to reduce the production cost of TPA while maintaining the quality of TPA at a certain level. Namely, the highly pure TPA having the same quality as in TPA produced in Comparative Example 6 can be obtained in the same process as in Example 2. As seen from Table 1 and Table 5, both the product of Example 2 and the product of Comparative Example 6 have the same transmissivity and give polyester of the same colour tone (b-value).

Although the content of 4CBA in TPA obtained in Example 2 is as high as 1050 ppm, the colour tone (b-value) of polyester prepared therefrom is in the same level as that of the polyester prepared from TPA obtained in Comparative Example 6. In addition, the amount of combusted acetic acid as the solvent in Example 2 is as low as 1.0 which is only about one half of that of Comparative Example 6 (namely, 1.9). These Production of TPA containing about 280 ppm of 4CBA Production of TPA was carried out in the same apparatus under the same conditions as in Example 1 except for using a catalyst containing reduced amounts of the respective components thereof, namely in concentrations, 200 ppm of cobalt, 200 ppm of manganese and 600 ppm of bromine in the reaction system; carrying out the main oxidation at 200° C. and the additional oxidation at about 193° C.; and subjecting a slurry of the reaction mixture obtained after finishing the additional oxidation to a second additional oxidation described below.

In the second additional oxidation, the pressure of the reaction mixture drawn out from the reactor for the additional oxidation was raised to 65 kg/cm$^2$ G by a pressure-raising pump, the temperature thereof was raised to 275° C. by passing the treated reaction mixture (as a slurry) through a monotubular heater and then, the reaction mixture was supplied to the reactor of the same type as that of the reactor for the additional oxidation and was subjected to the second additional oxidation at 275° C. under a pressure of 65 kg/cm$^2$ therein in a resident time of 30 min by supplying air thereinto at a rate of 0.07 part/hour. The results are shown in Table 6.

As is seen in Table 6, the effect of the present invention is exhibited also in the case where after oxidizing the greater part of the supplied p-xylene in the main oxidation and further oxidizing a reaction mixture in the first additional oxidation at a lower temperature, the resultant mixture is further oxidized in the second additional oxidation at a higher temperature to obtain a highly pure TPA containing about 280 ppm of 4CBA.

TABLE 6

| | Amount of recycled exhaust gas[1] | Reaction pressure (kg/cm$^2$G) | Partial pressure of O$_2$ (atm) | Ratio of inert gas pressure to vapour pressure | Transmissivity of TPA (T$_{340}$)[2] (%) | Content of 4CBA in TPA (ppm) | Amount of combusted acetic acid[3] | Colour tone of polyester[4] (b-value) |
|---|---|---|---|---|---|---|---|---|
| Example 10 | 0.5 | 19.5 | 0.53 | 0.79 | 93 | 280 | 1.0 | 2.8 |
| Example 11 | 1.0 | 23.0 | 0.73 | 1.09 | 94 | 270 | 1.0 | 2.8 |
| Comparative | 0 | 16.0 | 0.32 | 0.49 | 88 | 280 | 1.0 | 4.4 |

TABLE 6-continued

| | Amount of recycled exhaust gas[1] | Reaction pressure (kg/cm²G) | Partial pressure of $O_2$ (atm) | Ratio of inert gas pressure to vapour pressure | Transmissivity of TPA $(T_{340})$[2] (%) | Content of 4CBA in TPA (ppm) | Amount of combusted acetic acid[3] | Colour tone of polyester[4] (b-value) |
|---|---|---|---|---|---|---|---|---|
| Example 8 Comparative Example 9 | 0.2 | 17.5 | 0.41 | 0.61 | 90 | 290 | 1.0 | 4.0 |

What is claimed is:

1. A process for producing terephthalic acid from p-xylene continuously, wherein p-xylene is oxidized to terephthalic acid by air in the presence of a catalyst containing cobalt, manganese and bromine at a temperature of 180° to 230° C. in a water containing acetic acid solvent in which the concentration of oxygen gas contained in an exhaust gas obtained from the reaction vessel used for oxidizing p-xylene is 2 to 8% by volume, said process comprising:
   (a) preparing an oxidation exhaust gas by condensing a gas withdrawn from said reaction vessel for removing condensates from said gas;
   (b) dividing the prepared oxidation exhaust gas into a discharged gas and a recycled gas, in which the volume ratio of said recycled gas to said discharged gas is 0.3 to 5, said discharged gas being exhausted to the outside of the reaction system;
   (c) supplying continuously said recycled gas to the liquid phase of said reaction vessel; and
   (d) carrying out the oxidation reaction of p-xylene under reaction pressure higher than the pressure of the reaction system when gas is not recycled to the system.

2. The process of claim 1, in which the pressure ratio of a non-condensable gas to a condensable gas in the gas phase of the reaction vessel is regulated at 0.65 to 3.

3. The process of claim 1, in which the supply amount of the recycled gas is regulated so that the partial pressure of oxygen gas in the gas phase of the reaction vessel is 1.3 to 5 times as high as that of the reaction condition unsupplied with said recycled gas.

4. The process of any one of claims 1 to 3, in which the water content in the reaction system for oxidation of p-xylene is regulated at 7 to 14% by weight.

5. The process of any one of claims 1 to 3, in which the oxidation reaction is carried out at a temperature of 180° to 220° C.

6. The process of any one of claims 1 to 3, in which the concentration of oxygen in the oxidation exhaust gas is regulated at 4 to 7% by weight.

7. The process of any one of claims 1 to 3, in which the volume ratio of the recycled gas to the discharged gas is regulated at 0.5 to 3.

8. The process of claim 2, in which the pressure ratio of a non-condensable gas to a condensable gas is regulated at 0.7 to 2.

9. The process of claim 3, in which the partial pressure of oxygen gas in the gas phase of the reaction vessel is 1.5 to 3 times as high as that of the reaction condition unsupplied with the recycled gas.

* * * * *